(12) United States Patent
Rosencwaig et al.

(10) Patent No.: US 6,930,771 B2
(45) Date of Patent: Aug. 16, 2005

(54) OPTICAL INSPECTION EQUIPMENT FOR SEMICONDUCTOR WAFERS WITH PRECLEANING

(75) Inventors: Allan Rosencwaig, Danville, CA (US); Lanhua Wei, Fremont, CA (US)

(73) Assignee: Therma-Wave, Inc., Fremont, CA (US)

( * ) Notice: Subject to any disclaimer, the term of this patent is extended or adjusted under 35 U.S.C. 154(b) by 0 days.

(21) Appl. No.: 10/717,316

(22) Filed: Nov. 19, 2003

(65) Prior Publication Data

US 2004/0100633 A1 May 27, 2004

Related U.S. Application Data

(63) Continuation of application No. 09/294,869, filed on Apr. 20, 1999, now Pat. No. 6,714,300.
(60) Provisional application No. 60/102,167, filed on Sep. 28, 1998.

(51) Int. Cl.[7] .............................................. G01N 21/00
(52) U.S. Cl. .............................. 356/237.1; 356/237.2; 356/237.3
(58) Field of Search ........................ 356/237.1, 237.2, 356/237.3, 237.4, 237.5, 369, 432

(56) References Cited

U.S. PATENT DOCUMENTS

| | | | |
|---|---|---|---|
| 3,887,392 A | 6/1975 | Tang .............................. 134/1 |
| 5,261,965 A | * 11/1993 | Moslehi .......................... 134/1 |
| 5,306,671 A | 4/1994 | Ogawa et al. ............... 437/225 |
| 5,316,970 A | 5/1994 | Batchelder et al. ....... 250/423 P |
| 5,439,596 A | 8/1995 | Ohmi et al. ................. 210/748 |
| 5,449,411 A | 9/1995 | Fukuda et al. ......... 118/723 MP |
| 5,652,657 A | * 7/1997 | Yoshii et al. ................ 356/394 |
| 5,798,837 A | * 8/1998 | Aspnes et al. ............... 356/369 |
| 5,825,470 A | * 10/1998 | Miyai et al. ................... 355/72 |
| 6,038,015 A | * 3/2000 | Kawata ......................... 355/67 |
| 6,325,078 B2 | 12/2001 | Kamieniecki ................ 134/1.3 |

FOREIGN PATENT DOCUMENTS

| | | | |
|---|---|---|---|
| JP | 10-137704 | 11/1996 | ............. B08B/3/12 |
| JP | 4-357836 | 12/1999 | ......... H01L/21/304 |
| WO | WO 95/00681 | 1/1995 | ............ C23G/1/00 |
| WO | WO 98/05066 | 2/1998 | .......... H01L/21/66 |
| WO | WO 99/35677 | 7/1999 | ......... H01L/21/306 |

OTHER PUBLICATIONS

K. Imen et al "Laser assisted micron scale particle removal," App. Phys. Lett., vol. 58, No. 2, Jan. 14, 1991, pp. 203–205.*
K. Imen et al., "Laser–assisted micron scale particle removal," App. Phys. Lett., vol. 58, No. 2, Jan. 14, 1991, pp. 203–205.

* cited by examiner

Primary Examiner—Gregory J. Toatley, Jr.
Assistant Examiner—Roy M. Punnoose
(74) Attorney, Agent, or Firm—Stallman & Pollock LLP

(57) ABSTRACT

A method for improving the measurement of semiconductor wafers is disclosed. In the past, the repeatability of measurements was adversely affected due to the unpredictable growth of a layer of contamination over the intentionally deposited dielectric layers. Repeatability can be enhanced by removing this contamination layer prior to measurement. This contamination layer can be effectively removed in a non-destructive fashion by subjecting the wafer to a cleaning step. In one embodiment, the cleaning is performed by exposing the wafer to microwave radiation. Alternatively, the wafer can be cleaned with a radiant heat source. These two cleaning modalities can be used alone or in combination with each other or in combination with other cleaning modalities. The cleaning step may be carried out in air, an inert atmosphere or a vacuum. Once the cleaning has been performed, the wafer can be measured using any number of known optical measurement systems.

7 Claims, 3 Drawing Sheets

PRE-CLEAN CONTAMINATION LAYER RANGED FROM 0.5Å TO 1.1Å DEPENDING ON EXPOSURE TIME BETWEEN CLEANING CYCLES.

OPTICAL INSPECTION EQUIPMENT FOR SEMICONDUCTOR WAFERS WITH PRECLEANING

PRIORITY

This Application is a continuation of U.S. patent application Ser. No. 09/294,869, filed Apr. 20, 1999 now U.S. Pat. No. 6,714,300, which claimed the benefit of U.S. Provisional Application No. 60/102,167, filed Sep. 28, 1998, said application being incorporated herein by reference.

TECHNICAL FIELD

The subject invention relates to optical inspection equipment used to evaluate parameters of thin films on semiconductor wafers. The subject device includes a cleaning module for reducing contaminants on the surface of the wafer prior to measurement to improve the accuracy and repeatability of the optical measurements. In the preferred embodiments, the cleaning module includes either or both of a microwave radiation source and a radiant heating source.

BACKGROUND OF THE INVENTION

For many years, devices have existed for evaluating parameters of a semiconductor wafer at various stages during fabrication. There is a strong need in the industry to evaluate the parameters of multiple-layer thin film stacks on wafers using non-contact optical metrology tools. In these devices, a probe beam of radiation is directed to reflect off the sample and changes in the reflected probe beam are monitored to evaluate the sample.

One class of prior measurement devices relied on optical interference effects created between the layers on the sample or the layer and the substrate. In these devices, changes in intensity of the reflected probe beam caused by these interference effects are monitored to evaluate the sample. In many applications, the probe beam is generated by a broad band light source and such equipment is generally known as spectrophotometers.

In another class of instruments, the change in polarization state of the reflected probe beam is monitored. These devices are known as ellipsometers.

As thin films and thin film stacks have become more numerous and complex, the industry has begun developing composite measurement tools that have multiple measurement modules within a single device. One such tool is offered by the assignee herein under the name Opti-Probe 5240. This device includes a number of measurement modules including a broad band spectrophotometer and a single wavelength, off-axis ellipsometer. The device also includes a broadband rotating compensator ellipsometer as well as a pair of simultaneous multiple angle of incidence measurement modules. The overall structure of this device is described in U.S. Pat. No. 5,798,837, issued Aug. 25, 1998. The Opti-Probe device is capable of measuring information about ultra-thin films and thin film stacks with a high degree of precision.

There is a trend in the semiconductor industry to utilize very thin layers. For example, today, gate dielectrics can have a thickness less than 20 Å. It is anticipated that even thinner layers will be used. There is a need to measure the thickness of these very thin layers with a precision and repeatability to better than 0.1 Å. While the Opti-Probe device is capable of making such measurements with the necessary precision, problems have arisen with respect to repeatability, especially with ultrathin films. Repeatability means that if the same measurement is made at two different times, the same result for layer thickness will be produced.

After considerable investigation, it has been determined that variations in measurements over time is strongly affected by atmospheric conditions such as temperature, humidity and exposure time to the air. For example, the measured layer thickness could be considerably higher when the humidity is relatively high. The variation in measurement due solely to atmospheric conditions can exceed 1 Å which substantially reduces the likelihood of making repeatable measurements with a precision of 0.1 Å or better.

It is believed that the variation in measurements is due to the growth of a layer of hydrocarbons on the surface of the wafer. It is believed that this growth is related to water molecules that attach to the wafer surface when the wafer is exposed to normal atmospheric conditions. Since water is a polar molecule, we believe it may attract hydrocarbon molecules such that the contamination layer is actually associated with water. In order to improve the repeatability of the measurements results, it would be desirable to remove the contaminant layer prior to measurement.

There are many types of wafer cleaning procedures used in a semiconductor fabrication facility. However, any cleaning procedures which requires contact with the wafer, such as cleaning solutions, would not be desirable at this stage of fabrication since it can damage or contaminate the gate dielectric or the wafer. Additionally, most chemical cleaning processes require a drying cycle during which time a new hydrocarbon contamination layer could reform. High temperature baking is a non-contact cleaning approach that could be used to drive off a contaminant layer. However, the temperature required to clean the wafer would be relatively high and this high temperature can damage the gate dielectric.

Accordingly, it is an object of the invention to provide a method of evaluating a semiconductor wafer which includes an initial cleaning step that does not have the drawbacks of the prior art approaches.

It is a further object of the subject invention to provide a new and improved optical metrology system which utilizes microwave excitation to clean contaminants off the wafer prior to or during measurement to improve the repeatability of the result.

It is still a further object of the subject invention to provide a new and improved optical metrology system which utilizes radiant heating to clean contaminants off the wafer prior to or during measurement to improve the repeatability of the result.

It is still another object of the subject invention to provide a cleaning system wherein microwave radiation and radiant heating can be combined to enhance the cleaning the effect.

It is still another object of the subject invention to provide a microwave or radiant heating cleaning system which can be combined with one or more additional cleaning modalities such as conductive heating, UV radiative cleaning or carbon dioxide pellet cleaning.

SUMMARY OF THE INVENTION

In accordance with these and other objects, the subject invention provides for a method and apparatus for analyzing the characteristics of a semiconductor wafer. In the invention, the wafer is subjected to microwave radiation or radiant heating for a time period sufficient to significantly and repeatably reduce the thickness of any layer of water related contamination which may be on the wafer.

When microwave energy is used, it may be pulsed to increase the localized heating while minimizing the overall heating of the wafer. The microwave treatment can be performed in air, or in an atmosphere of an inert gas such as nitrogen or in a vacuum.

Once the wafer has been treated by the microwave radiation or radiant heating, it can be measured using a conventional optical metrology tool. As described above, one or more probe beams are caused to reflect off the sample and changes in the reflected probe beam or beams are monitored to derive information about the sample. It may be desirable to perform the measurement in a vacuum or inert gas environment. It may also be desirable to make the measurement in the same chamber where the wafer was exposed to the cleaning step to minimize any build up of the contamination layer while the wafer is being transferred. It would also be possible to measure the wafer at the same time it is being exposed to the microwave radiation or radiant heating.

It is believed that the cleaning achieved using the microwave radiation is not purely a thermal effect. Rather, the microwave radiation excites the rotational bands of the water molecules helping to drive it into the vapor state thereby carrying off any associated hydrocarbon contamination.

If a radiant heat source is used, it should operate in the one to ten micron wavelength regime. It is believed that the cleaning effect achieved using a radiant heat source at this wavelength excites the vibrational bands in the water molecules helping to drive it into the vapor state thereby carrying off any associated hydrocarbon contamination.

In one embodiment of the invention, cleaning is achieved by combining the microwave radiation and the radiant heating. Using two cleaning sources permits the optimization of the parameters of both modalities to maximize cleaning while minimizing damage to the wafer or deposited thin films.

As discussed in more detail below, in certain situations, it may be beneficial to enhance the microwave or radiant heat cleaning of the wafer with other cleaning modalities. For example, supplemental heating of the wafer may be performed using a conductive or convection heat source. Certain other contaminants might be removed by bombardment of the wafer with UV radiation or a stream of frozen carbon dioxide pellets. Any of these cleaning modalities could be used alone or in combination with microwave or radiant heating to clean the wafer prior to measurement.

It may also be desirable to initially expose the wafer to a high humidity environment before cleaning the wafer with microwave energy. Such a high humidity environment would increase the amount of water molecules attached to the wafer. When the wafer is subsequently exposed to the microwave radiation, the vaporization of these added water molecules may actually enhance the removal of other contaminants thereby improving the cleaning action.

Further objects and advantages of the subject invention will become apparent from the following detailed description, taken in conjunction with the drawings, in which:

DETAILED DESCRIPTION OF THE PREFERRED EMBODIMENTS

Figure 1:
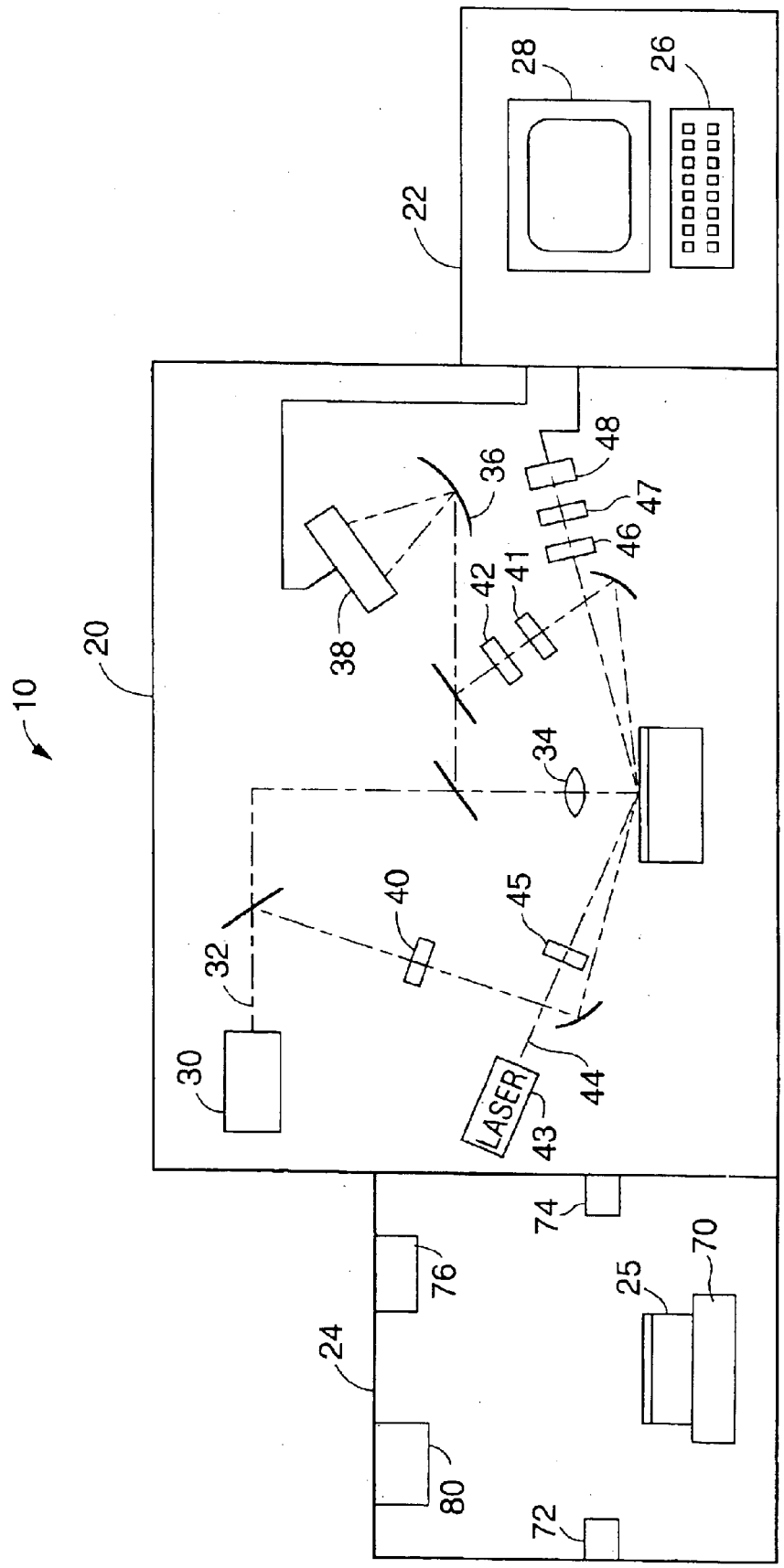
FIG. 1 is a schematic diagram of a measurement device in accordance with the subject invention.

FIG. 1 is a simplified block diagram of a device 10 made in accordance with the subject invention. This device includes a measurement station 20 and a computer processor acting as a controller and computational module 22. In the preferred embodiment, the device also includes a microwave or radiant heating module 24 for holding a wafer 25. It should be noted that in the broadest sense, the method of the subject invention can be performed with separate cleaning and optical measurement devices. However, there are many reasons why the two tools should be combined in a single instrument. For example, automatic wafer transport can be provided between the cleaning module and the measurement module. Besides eliminating human handling, direct wafer transfer can reduce the time between cleaning and measurement thereby minimizing the regrowth of a contaminant layer prior to the measurement. In addition, a single tool has a smaller footprint and therefore takes up less space in the semiconductor fabrication facility. A single device would also be less expensive than two separate devices.

The controller station 22 can include a convention processor (not shown), a data input device 26 and a display screen 28.

The measurement station 20 can include one or more of the known optical metrology techniques. FIG. 1 illustrates two such techniques in simplified form. More specifically, a broad band light source 30 is used to generate a probe beam 32 which is focused on the sample with a lens 34. The reflected probe beam is directed to a grating 36 and then to an array photodetector 38 for measuring the variations in intensity as a function of wavelength. This arrangement relies on optical interference effects caused by multiple reflections of the beam at the layer interfaces.

The measurement station 20 can also be arranged to perform ellipsometry. As shown in FIG. 1, some of the light from source 30 can be redirected by a beam splitter and turning mirrors to strike the sample at an oblique angle of incidence. The beam is first passed through a polarizer 40 to create a known polarization. After reflection off of the sample, the beam passes through a rotating compensator 41 and an analyzer 42 and is directed by another beam splitter to the grating 36 and photodetector 38. The detection stage of the ellipsometer functions to analyze the change in polarization state of the beam induced by reflection off of the sample. The spectrophotometer and spectroscopic ellipsometer measurements may be taken simultaneously or sequentially. The outputs from detector 38 for either or both measurements are supplied to the processor in the controller module 22 for evaluating the sample.

In the preferred embodiment, the measurement station will include additional measurement modules used either alone or in combination. U.S. Pat. No. 5,798,837, incorporated herein by reference, illustrates how such multiple measurement modules can be integrated into a single device. The cleaning concepts of the subject invention can be used to improve the repeatability of any of these measurement modalities.

One such additional measurement modality described in U.S. Pat. No. 5,798,837 is an off-axis, narrow band ellipsometer. Such a device is particularly useful for measuring the thickness of very thin films such as gate dielectrics. The basic elements of such an ellipsometer are also shown in FIG. 1. More specifically, the narrow-band light source can be a laser 43 emitting a probe beam 44. The probe beam is passed through a polarizer 45 and directed to strike the sample at an oblique angle of incidence. The reflected beam is passed through a rotating compensator 46 and an analyzer 47. The intensity of the reflected beam is then measured by photodetector 48. The output of photodetector 48 is supplied to the processor in the controller module 22. The output signals can be used alone or in combination with the signals from detector 38.

It is within the scope of the subject invention to utilize other conventional ellipsometer arrangements. For example, it is well known that ellipsometers measurements can be made if the analyzer 47 is rotated while the compensator 46 is held stationary.

In accordance with the method of the subject invention, the semiconductor wafer to be measured is first subjected to a cleaning step in module 24. The cleaning step is arranged to drive off a significant amount of the water molecules and associated contaminants to permit repeatable measurements.

In one preferred embodiment, the cleaning step is performed with microwave radiation. It is believed that the microwave radiation excites the rotational bands in the water molecules to drive it into the vapor state carrying off the associated hydrocarbon contaminants. There also may some secondary thermal effects due to the absorption of the microwave energy in the wafer through eddy currents. The parameters selected to perform the microwave heating step are interrelated and depend on the level of contamination, the time available for the cleaning step, the amount of temperature rise which the wafer can tolerate without damage and the level of microwave radiation that the gate dielectric can tolerate without adversely effecting the ultimate performance of any device fabricated from that wafer.

For example, if the microwave energy selected is relatively low, it will take a longer time to drive off the layer of contamination. Conversely, if the microwave energy is high, cleaning time will be shorter, but more heat might be generated causing damage to the wafer.

Another parameter which can be varied is the power or intensity of the microwave radiation. Decreasing the power may increase the time needed to clean the wafer but could prevent damage. As noted below, the level of microwave power needed to clean the wafer could be lowered if other cleaning modalities, such as radiant heating, are used as well. The proper selection of parameters and cleaning modality combinations can be empirically determined.

Figure 2:
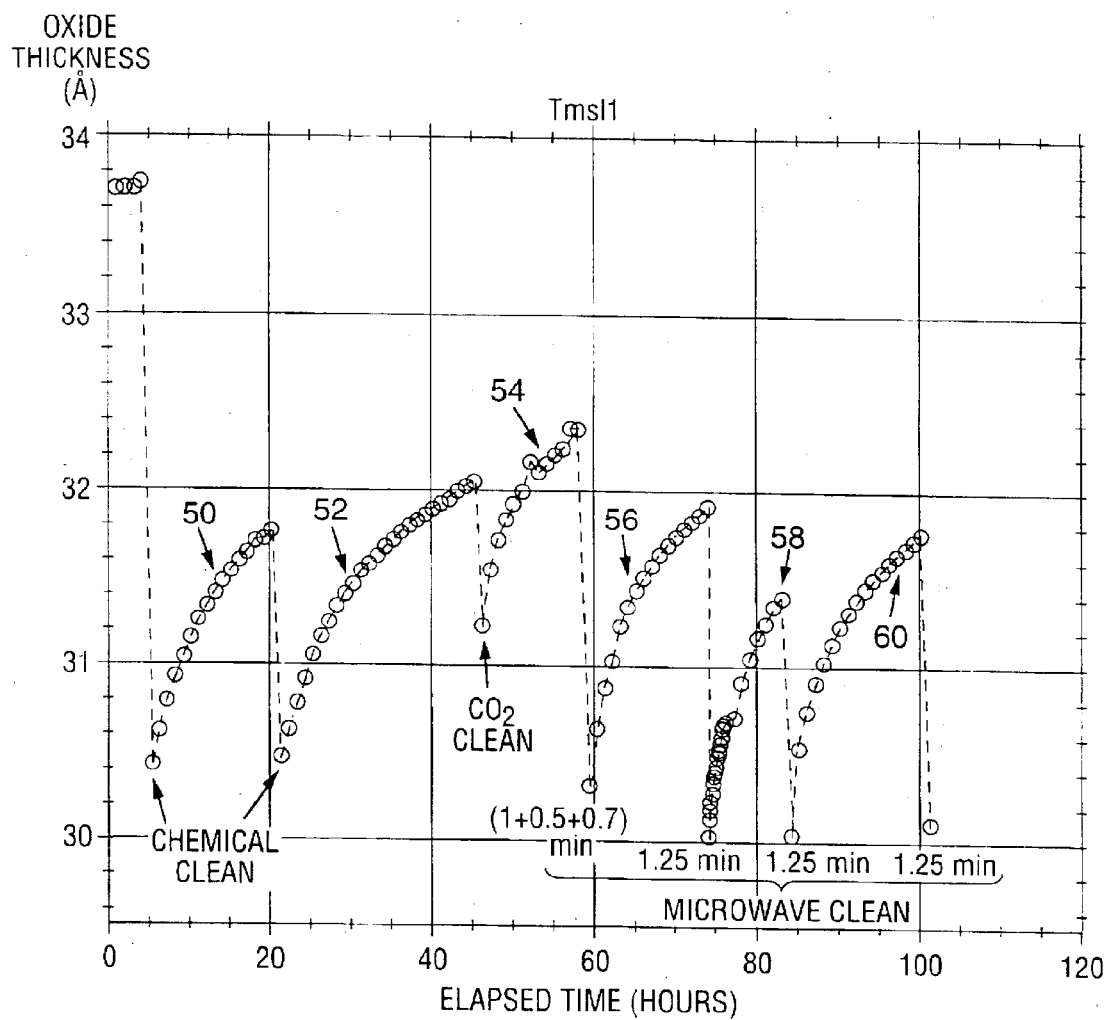
FIG. 2 is a graph of measurement results achieved using the subject invention.

In initial tests, wafers were subjected to microwave energy from a conventional 600 Watt microwave oven operating at 2.54 gigahertz for a period of between one to five minutes. FIG. 2 illustrates some of the results that were achieved with this process.

The horizontal axis in FIG. 2 represents elapsed time in hours. The vertical axis represents the thickness of a surface layer (oxide and contaminant layer) in Angstroms (Å) on a single test wafer. The thickness was measured using an off-axis, narrow band ellipsometer of the type shown in FIG. 1 and described in greater detail in U.S. Pat. No. 5,798,837. Each point on each curve represents a measurement on the wafer. The left most data point of each curve was taken after a cleaning step. As can be seen, after cleaning, the thickness of the contamination layer regrew by as much as two angstroms over a period of 15 to 20 hours (to about 32 Å).

The first two curves (50, 52) represent repeated measurements taken after an initial chemical cleaning step. The chemical cleaning step was performed with a liquid wafer cleaner made by Cole-Pamer Instrument Company, Micromodel 8790-00. After cleaning, the wafer is rinsed using de-ionized water. After the rinsing, the wafers had to go through a drying cycle for about 10 minutes before the thickness measurements could be taken.

As can be seen, the chemical cleaning step functioned to remove about a 1 to 1.5 Å contamination layer. (Compare the last data point of curve 50 to the first data point of curve 52.) In both tests, the measured thickness was reduced to about 30.5 Å. As will be seen below, the microwave cleaning approach was more effective.

Curve 54 represents repeated measurements taken after an initial cleaning step with carbon dioxide pellets. In this cleaning step, compressed carbon dioxide from a tank is channeled under pressure through a nozzle. The fast expanding gas creates a mixture of cooled carbon dioxide gas and pellets. The size of the nozzle can be adjusted to control the expansion rate of the gas. As can be seen, this cleaning approach was able to reduce the contamination layer thickness by about 1 Å to give an apparent oxide layer thickness of 31 Å.

The final three curves (56, 58 and 60) represent repeated measurements taken after an initial microwave cleaning step. The measurements on the first curve 56 were taken after the wafer had been subjected to three separate, consecutive microwave exposures of one minute, followed by 30 seconds, followed by 42 seconds (0.7 minutes). Using this approach, the thickness measurement was reduced by about 1.5–2 Å to about 30.3 Å. In the next two curves (58 and 60), the wafer was first subjected to continuous microwave excitation for a period of 1.25 minutes and then repeatedly measured. In each of the latter two cases, the layer thickness was reduced to 30 Å immediately after cleaning. The 30 Å thickness was less than the other two cleaning methods indicating that the microwave cleaning was the most effective.

As can be seen from curves 56, 58 and 60 in FIG. 2, after cleaning, the thickness of the contamination layer grew by about 1 to 2 Å over a period of 15 hours to 20 hours. Thus, the result for measured thickness would vary significantly depending on when the wafer was measured after cleaning. However, as illustrated by the last two curves (58 and 60), repeatable measurements of a thickness of 30 Å can be achieved if the wafer is measured immediately after sufficient microwave cleaning. The measurements should be taken within 15 minutes of the cleaning procedure. Preferably the measurement should be made as quickly as possible after cleaning.

Figure 3:
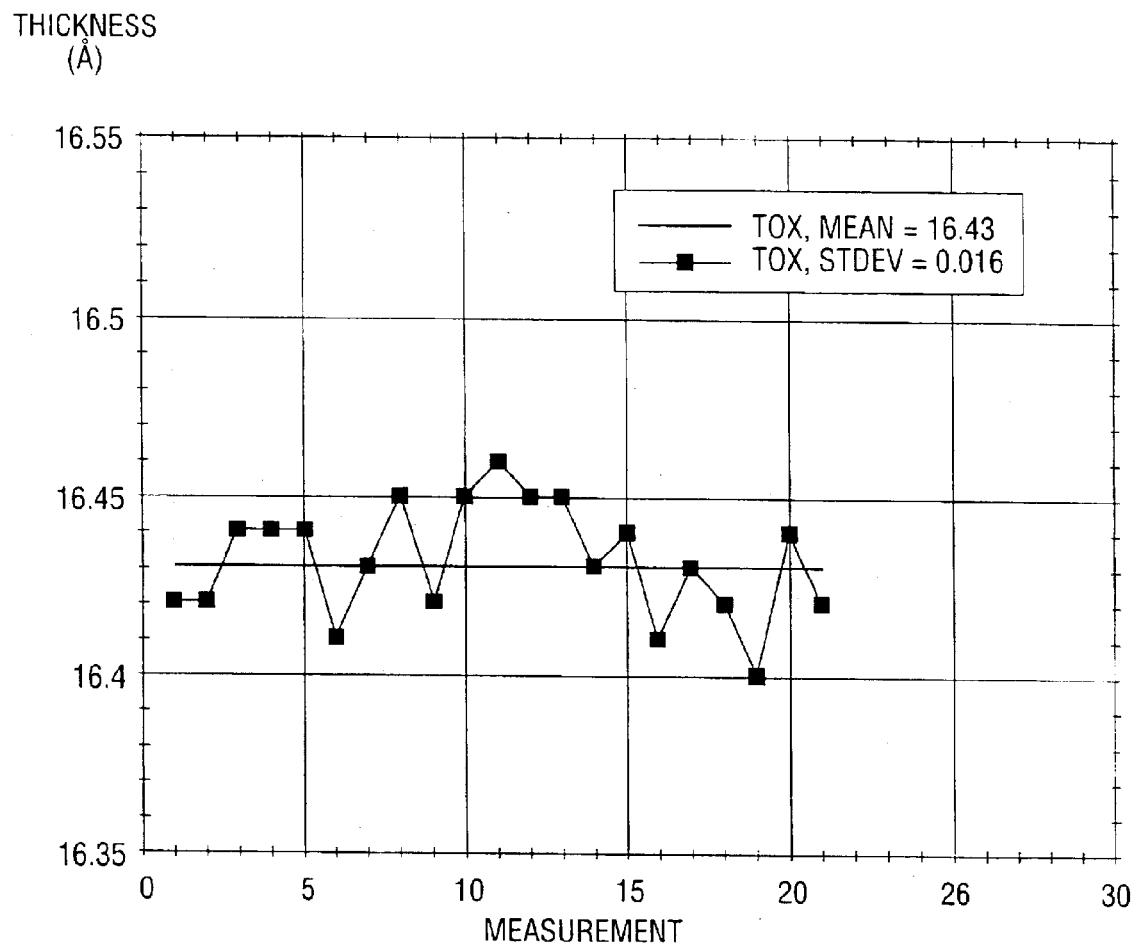
FIG. 3 is a graph of measurement results using microwave heating and demonstrates the repeatability of the cleaning procedure.

In addition, in subsequent experiments, it has been demonstrated that the microwave cleaning process is highly repeatable and appears to remove essentially all of the contamination layer on the wafer. As shown in FIG. 3, we have been able to achieve a thickness measurement repeatability after cleaning of better than 0.02 Å (one standard deviation) even though the contamination layer present before cleaning ranged in thickness from 0.5–1.1 Å. (The thickness of the contamination layer prior to cleaning was varied by varying the time between successive cleaning steps.)

It is believed that the effectiveness of the microwave cleaning may be increased by using a pulsed microwave system. Pulsing the microwave energy could minimize the time period in which heat can be conducted from the contamination layer to the wafer. Therefore, the peak power of the microwave energy can be increased to permit more vigorous cleaning. If pulsed microwave bursts are employed, it is believed that the pulses of microwave energy should be less than a few milliseconds and preferably in the microsecond regime. In this short time period, the heating should be limited to a layer of about 100 microns, the skin depth of doped silicon. This estimate is based on a resistivity of 10-2 ohm-cm and a microwave frequency of 2.54 gigahertz. This depth is only about ⅐ of the total wafer thickness so that the bulk of the wafer would not be heated.

Another approach to minimizing unwanted heating of the wafer would be to place the wafer on a heat sink 70 during microwave excitation. In this case, excess heat could flow out of the wafer into the heat sink.

It may also be desirable to initially expose the wafer to a high humidity environment before cleaning the wafer with microwave energy or radiant heating. Such a high humidity environment would increase the amount of water molecules attached to the wafer. These extra water molecules may collect in the crevices or spaces between and underneath the contaminant particles. When the wafer is subsequently exposed to the microwave radiation or radiant energy, the vaporization of these added water molecules may actually enhance the removal of other contaminants thereby improving the cleaning action.

Since it is believed that contaminants arise from the atmosphere, it may be desirable although, not necessary, to conduct the microwave or radiant heating cleaning step and/or the measurement step in either a vacuum or inert gas atmosphere rather than in air. For example, either or both of the cleaning station 24 and the measurement station 20 can be subjected to a vacuum. Alternatively, one or both of these stations could be filled with an inert gas such as nitrogen. Such steps will minimize the reformation of the contamination layer after cleaning and prior to measurement.

Another alternative is to subject the wafer to a flow of air or inert gas during the microwave cleaning step. Providing a gas flow past the wafer can help cool the wafer and facilitate the removal of the contaminant layer. The gas flow could be provided through an inlet 72 and an exhaust 74.

The cleaning effects of the microwave treatment can be enhanced if it is combined with other cleaning modalities. For example, some amount of heating from a separate source may function to enhance the microwave cleaning. One proposed form of heating is to use a radiant heat source 76 operating in the 1 to 10 micron wavelength regime. Such radiation can be generated by filament type heaters or other known sources such as a flashlamp. A heat source operating at these infrared wavelengths functions to excite the vibrational bands of water further helping to drive off the water molecules and associated hydrocarbon contaminants. Alternatively, conventional conductive or convective heat sources can be used to raise the temperature of the wafer. (A conductive heat source could be used in place of the heat sink 70). One advantage of combining microwave and heat cleaning modalities is that the intensity or power of either or both can be adjusted to maximize cleaning while minimizing damage to the wafer or thin films that can adversely effect the performance of any device fabricated from the wafer.

In another alternate embodiment, cleaning is performed with a radiant heat source as described above without microwave radiation. In initial experiments, a radiant heat source was successfully used by itself to reduce the contamination layer on the wafer.

Another alternative is to subject the wafer to UV radiation. It is known that UV radiation, particularly in combination with higher temperatures, can help remove an organic layer. Thus, it might prove possible to remove the hydrocarbon layer with a continuous exposure to UV radiation as from a deuterium light source, or a pulsed UV light source or a laser light source such as an excimer laser (Shown generically at 80).

A still further approach to enhance the microwave or radiant cleaning procedure is to use frozen carbon dioxide pellet cleaning. This approach is gaining popularity as a dry cleaning process for the removal of hydrocarbons, residual resist and other layers and for the removal of particles from the surface of the wafer.

In the frozen $CO_2$ pellet process, a stream of very small, frozen $CO_2$ particles is directed onto the surface of a wafer. Due to the relatively higher temperature of the wafer, the pellets immediately vaporize upon contact with the wafer surface. The rapid vaporization drives off the surface contamination layer. The $CO_2$ pellet cleaning could be set up in the cleaning station 24.

In summary, there has been disclosed an improved method and apparatus for evaluating the parameters of a semiconductor wafer. In this approach, the hydrocarbon contamination layer is substantially reduced using a cleaning step. In one embodiment, the cleaning step consists of exposing the wafer to microwave radiation. In another embodiment, the wafer is exposed to radiant heating. Either approach used alone, or in combination, improves the repeatable of the measurements which can be made.

While the subject invention has been described with reference to the preferred embodiments, various changes and modifications could be made therein, by one skilled in the art, without varying from the scope and spirit of the subject invention as defined by the appended claims.

We claim:

1. An apparatus for evaluating a semiconductor wafer comprising:

an optical inspection system for analyzing characteristics of a wafer, said optical ispection including at least one or more of the type selected from the group consisting of a spectrophotometer, a spectroscopic ellipsometer and a narrow band ellipsometer; and a cleaning system for cleaning a wafer operatively coupled to the optical inspection system, said cleaning system including at least one or more of the modalities selected from the group consisting of microwave excitation, radiant heating, conductive heating and optical radiation, said cleaning system functioning to reduce contaminants on the wafer so that the analysis of the wafer by the optical inspection system can be more accurate.

2. An apparatus as recited in claim 1, wherein the optical inspection system and the cleaning system are located in adjacent but separate modules.

3. An apparatus as recited in claim 2, further including a wafer transport module coupled to the cleaning module and the optical inspection module which operates to transport a wafer cleaned by the cleaning module to the optical inspection module.

4. An apparatus as recited in claim 1, wherein the optical inspection system and the cleaning system are located in the same chamber.

5. An apparatus as recited in claim 4, wherein the optical radiation used for the cleaning system is defined by UV radiation.

6. An apparatus as recited in claim 1, wherein the optical radiation used for the cleaning system is defined by UV radiation.

7. An apparatus as recited in claim 1, wherein the cleaning system includes a conductive heat source.

* * * * *